(12) United States Patent
Richardson

(10) Patent No.: US 8,252,766 B2
(45) Date of Patent: *Aug. 28, 2012

(54) USE OF SPONGOSINE FOR THE TREATMENT OF PAIN

(75) Inventor: Peter Richardson, Cambridge (GB)

(73) Assignee: CBT Development Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/537,564

(22) PCT Filed: Dec. 9, 2003

(86) PCT No.: PCT/GB03/05379
§ 371 (c)(1),
(2), (4) Date: Aug. 28, 2006

(87) PCT Pub. No.: WO2004/052377
PCT Pub. Date: Jun. 24, 2004

(65) Prior Publication Data
US 2007/0010475 A1    Jan. 11, 2007

(30) Foreign Application Priority Data
Dec. 9, 2002  (GB) .................................. 0228723.3

(51) Int. Cl.
*A61K 31/70*    (2006.01)
(52) U.S. Cl. ...................................................... 514/46
(58) Field of Classification Search .................... 514/46; 536/27.63
See application file for complete search history.

(56) References Cited

U.S. PATENT DOCUMENTS

| | | | |
|---|---|---|---|
| 3,936,439 A | 2/1976 | Marumoto et al. | |
| 4,225,591 A | 9/1980 | Marumoto et al. | |
| 4,255,565 A | 3/1981 | Marumoto et al. | |
| 4,705,758 A | 11/1987 | Bruns | |
| 5,104,859 A * | 4/1992 | Sollevi | 514/46 |
| 5,140,015 A | 8/1992 | Olsson et al. | |
| 5,231,086 A * | 7/1993 | Sollevi | 514/46 |
| 5,506,213 A | 4/1996 | Carson et al. | |
| 5,596,094 A | 1/1997 | Prashad et al. | |
| 5,677,290 A * | 10/1997 | Fukunaga | 514/46 |
| 5,679,649 A * | 10/1997 | Fukunaga | 514/46 |
| 5,679,650 A * | 10/1997 | Fukunaga et al. | 514/46 |
| 5,683,989 A * | 11/1997 | Lau et al. | 514/46 |
| 5,731,296 A * | 3/1998 | Sollevi | 536/46 |
| 5,877,180 A | 3/1999 | Linden et al. | |
| 5,942,497 A * | 8/1999 | Fukunaga et al. | 514/46 |
| 6,004,945 A * | 12/1999 | Fukunaga | 514/46 |
| 6,110,902 A | 8/2000 | Mohler et al. | |
| 6,180,616 B1 * | 1/2001 | Fukunaga | 514/46 |
| 6,544,960 B1 | 4/2003 | Eldred et al. | |
| 6,642,209 B1 * | 11/2003 | Fukunaga | 514/46 |
| 7,759,321 B2 * | 7/2010 | Richardson et al. | 514/46 |
| 7,790,698 B2 * | 9/2010 | Richardson | 514/46 |
| 2004/0110718 A1 | 6/2004 | Devos et al. | |

FOREIGN PATENT DOCUMENTS

| | | |
|---|---|---|
| AU | 49412/72 | 5/1974 |
| CN | 1147815 A | 4/1997 |
| DE | 2258378 | 6/1973 |
| EP | 0983768 | 3/2000 |
| FR | 2162128 | 7/1973 |
| GB | 2396108 | 3/1946 |
| JP | A-49-80096 | 8/1974 |
| JP | A-54-61194 | 5/1979 |
| JP | A-54-61195 | 5/1979 |
| JP | A-48-61498 | 1/2012 |
| WO | WO91/13082 | 9/1991 |
| WO | WO9113082 | 9/1991 |
| WO | WO94/23723 | 10/1994 |
| WO | WO95/29680 | 11/1995 |
| WO | WO95/30683 | 11/1995 |
| WO | WO 9638728 | 12/1996 |
| WO | WO99/06053 | 2/1999 |
| WO | WO99/11274 | 3/1999 |
| WO | WO 9934804 | 7/1999 |
| WO | WO00/77018 | 12/2000 |
| WO | WO02/18404 | 3/2002 |
| WO | WO2004/052377 | 6/2004 |
| WO | WO2004/056181 | 7/2004 |
| WO | WO2004/078183 | 9/2004 |
| WO | WO2004/078184 | 9/2004 |

(Continued)

OTHER PUBLICATIONS

Ueeda et al., "Cardiovascular Actions of Adenosines, But Not Adenosine Receptors, Differ in Rat and Guinea Pig," Life Sciences, 49(18), 1351-1358 (1991).*

(Continued)

*Primary Examiner* — Lawrence E Crane
(74) *Attorney, Agent, or Firm* — Fish & Richardson P.C.

(57) ABSTRACT

The compound spongosine (2-methoxyadenosine), of the class of adenosines, is useful as an analgesic, particularly in a method of preventing, treating, or ameliorating pain which comprises administering spongosine (2-methoxyadenosine) to a subject in need of such prevention, treatment, or amelioration.

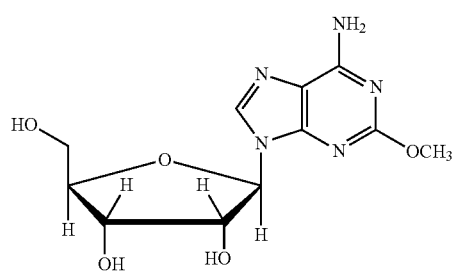

Spongosine (2-methoxyadenosine)

40 Claims, 5 Drawing Sheets

FOREIGN PATENT DOCUMENTS

| WO | WO 2004079329 | 9/2004 |
|---|---|---|
| WO | WO2005/084653 | 9/2005 |
| WO | WO2007/077018 | 7/2007 |

OTHER PUBLICATIONS

Makujina et al., "Structure-Activity Relationship of 2-(ar)alkoxyadenosines at the Adenosine Receptor in Coronary Artery," European Journal of Pharmacology, 243(1), 35-38 (1993).*
Herrick-Davis et al., "Evaluation of Adenosine Agonists as Potential Analgesics," European Journal of Pharmacology, 162(2), 365-369 (Mar. 21, 1989): only Science Direct abstract supplied.*
Karlsten et al., "The Antinociceptive Effect of Intrathecally Administered Adenosine Analogs in Mice Correlates with the Affinity for the A1-Adenosine Receptor," Neuroscience Letters, 121(1-2), 267-270 (Jan. 2, 1991): only Science Direct Abstract supplied.*
Venes et al.(eds.) (I), Taber's Cyclopedic Medical Dictionary, 19th Edition, F. A. Davis Co., Philadelphia, PA, 2001, see pp. 665-667, see the definition of "edema:" supplied by applicant.*
Anon., "What is Pain Medicine?" American Board of Pain Medicine, Exhibit A, accessed on line at <http://www.abpm.org/what/index.html> on Oct. 28, 2007: supplied by applicant.*
Venes et al.(eds.) (II), Taber's Cyclopedic Medical Dictionary, 19th Edition, F. A. Davis Co., Philadelphia, PA, 2001, see pp. 1092-1094 and 1552-1557, see the definitions of "inflammation" and "pain."*
Oei et al., "Correlation Between Binding Affinities for Brain A1 and A2 Receptors of Adenosine Agonists and Antagonists and Their Effects on Heart Rate and Coronary Vascular Tone," J. Pharmacology and Experimental Therapeutics, 247(3), 882-888 (1988).*
Ribeiro et al., "Adenosine Receptors in the Nervous System: Pathophysiological Implications," Progress in Neurobiology, 68, 377-392 (2003).*
Silverman, R. B., "Bioisosterism," part of Chapter 2 of "The Organic Chemistry of Drug Design and Drug Action," Academic Press, 1992, New York, NY, only pp. 4 and 19-23 supplied.*
"Aldrich Handbook of Fine Chemicals and Laboratory Equipment," 1015-1016, (2000); XP002366927.
Askalan, R. et al., "Role of Histidine Residues in the Adenosine A2A Receptor Ligand Binding Site," Journal of Neurochemistry, 63(4):1477-84, (1994); XP001196996.
Bartlett, R. et al., "Synthesis and Pharmacological Evaluation of a Series of Analogues of 1-Methylisoguanosine," Journal of Medicinal Chemistry, 24:947-54, (1981); XP002225573.
Belardinelli, L. & Isenberg, G., "Isolated Atrial Myocytes: Adenosine and Acetylcholine Increase Potassium Conductance," The American Journal of Physiology, 224:H734-H737, (1983).
Belfrage, M. et al., "The Safety and Efficacy of Intrathecal Adenosine in Patients with Chronic Neuropathic Pain," Anesthesia and Analgesia, 89(1):136-42, (1999); XP009027670.
Bhakuni, D., "Biological Activity of Marine Nucleosides and their Analogues," Proceedings of the Indian National Science Academy. Part B Biological Sciences, 65(Part 2):97-112, (1995); XP001165752.
Bressi, J. et. al., "Adenosine Analogues as Inhibitors of Trypanosoma Brucei Phosphoglycerate Kinase: Elucidation of a Novel Binding Mode for a 2-Amino-N6-Substituted Adenosine," Journal of Medicinal Chemistry, 43(22):4135-50, (2000); XP000999137.
Collins, S. et al., "The Effect of GR190178, a Selective Low-Efficacy Adenosine A1 Receptor Agonist, on the Treatment of Neuropathic Hyperalgesia in the Rat," British Journal of Pharmacology, 133(Proceedings Supplement):48p (2001), Proceedings of the British Pharmacological Society Meeting, (Dec. 18-21, 2000); XP009027671.
Daly, J. et al., "Structure-Activity Relationships for N6-Substituted Adenosines at a Brain A1-Adenosine Receptor with a Comparison to an A2-Adenosine Receptor Regulating Coronary Blood Flow," Biochemical Pharmacology, 35(15):2467-81 (1986) XP009010090.
Dan, K., "Nerve Block Therapy and Postherpetic Neuralgia," Critical Reviews in Physical and Rehabilitation Medicine, 7(2):93-112 (1995) Embase Database Accession No. EMB-1995373280. XP002273335.
De Zwart, M. et al., "5'-N-Substituted Carboxamidoadenosines as Agonists for Adenosine Receptors," Journal of Medicinal Chemistry, 42(8): 1384-92 (1999) XP001002032.
Deghati, P. et al., "Regioselective Nitration of Purine Nucleosides: Synthesis of 2-Nitroadenosine and 2-Nitroinosine," Tetrahedron Letters, 41(8):1291-5 (2000) XP004188609.
Feoktistov, I. et al., "Adenosine A2B Receptors: A Novel Therapeutic Target in Asthma?," Trends in Pharmacological Sciences, 19(4):148-53 (1998) XP002287445.
Fishman, P. et al., "A3 Adenosine Receptor as a Target for Cancer Therapy," Anti-Cancer Drugs, 13(5):437-43 (2002) XP009024520.
Hiley, C. et al., "Effects of pH on Responses to Adenosine, CGS 21680, Carbachol and Nitroprusside in the Isolated Perfused Superior Mesenteric Arterial Bed of the Rat," British Journal of Pharmacology, 116(6):2641-2646 (1995) XP008032448.
Jiang, Q. et al., "Mutagenesis Reveals Structure-Activity Parallels Between Human A2A Adenosine Recveptors and Biogenic Amine G Protein-Coupled Receptors," Journal of Medicinal Chemistry, 40(16):2588-95 (1997) XP002287314.
Kaul, P. et al., "Adenosine Agonist of Marine Origin Indicative of Two Types of Adenosinergic Receptors," Pharmacologist, 23(3):540 (1981) XP009027638.
Keeling, S. et al., "The Discovery and Synthesis of Highly Potent, A2a Receptor Agonists," Bioorganic and Medicinal Chemistry Letters, 10(4):403-6 (2000) XP004189943.
Kirk, I. et al., "Further Characterization of [3H]-CGS 21680 Binding Sites in the Rat Striatum and Cortex," British Journal of Pharmacology, 114(2):537-43 (1995) XP008032472.
Klitgaard, H. et al., "Contrasting Effects of Adenosine $A_1$ and $A_2$ Receptor Ligands in Different Chemoconclusive Rodent Models," European Journal of Pharmacology, 242:221-8 (1993).
Knabb, R. et al., "Consistent Parallel Relationships Among Myocardial Oxygen Consumption, Coronary Blood Flow, and Pericardial Infusate Adenosine Concentration with Various Interventions and Beta-Blockade in the Dog," Circulation Research, 53:33-41 (1983).
König, G., "Meeresorganismen als Quelle Pharmazeutisch Bedeutsamer Naturstoffe," Deutsche Apotheker Zeitung, 132(14):673-83 (1992) XP002255617.
Marumoto, R. et al. "Synthesis and Coronary Vasodilating Activity of 2-Substituted Adenosines," Chemical and Pharmaceutical Bulletin, 23(4):759-74 (1975) XP002154408.
Matova, M. et al. "QSAR Analysis of 2-Alkyloxy and 2-Aralkyloxy Adenosine A1- and A2-Agonists," European Journal of Medicinal Chemistry, 32(6):505-13 (1997) XP004088461.
Matsuda et al., Nucleosides and Nucleotides. XXVII. Synthesis of 2- and 8-Cyanoadenosines and their Derivatives, Chemical and Pharmaceutical Bulletin, 27(1):183-92 (1979) XP002127436.
Matsuda, A. et al., "Nucleosides and Nucleotides. 103. 2-Alkyladenosines: a Novel Class of Selective Adenosine A2 Receptor Agonists with Potent Antihypertensive Effects," Journal of Medicinal Chemistry, 35:241-52 (1992) XP002170995.
Miles, R. et al., "Nucleic Acid Related Compounds," Journal of the American Chemical Society, 117:5951-7 (1995) XP002366161.
Nair, V. et al., "Novel, Stable Cogeners of the Antiretroviral Compound 2', 3'-Dideoxyadenosine," Journal of the American Chemical Society, 111(22):8502-4 (1989) XP001105896.
Ojha, L. et al., "A Simple Method for Synthesis of Spongosine, Azaspongosine, and their Antiplatelet Effects," Nucleosides and Nucleotiodes, 14(9-10):1889-1900 (1995) XP009027643.
Okusa, M., "A2A Adenosine Receptor: A Novel Therapeutic Target in Renal Disease," American Journal of Physiology, 282(1 Part 2):F10-F18 (2002) XP002287448.
Rieger, J.M. et al., "Design, Synthesis, and Evaluation of Novel A2A Adenosine Receptor Agonists," Journal of Medicinal Chemistry, 44:531-9 (2001) XP002222174.
Ribeiro, J. et al., "Adenosine Receptors in the Nervous System: Pathophysiological Implications," Progress in Neurobiology, 68(6):377-92 (2002) XP002287447.
Sawynok, J. "Adenosine Receptor Activation and Nociception," European Journal of Pharmacology, 317(1):1-11 (1998) XP002273334.
Schaeffer, H. et al., "Synthesis of Potential Anticancer Agents. XIV. Ribosides of 2, 6-Disubstituted Purines," Journal of the American Chemical Society, 80:3738-42 (1958) XP002300926.

Smith, J. et al., "The Effects of Reduced pH on A2B Adenosine Receptor-Evoked Cyclic AMP Generation in the Guinea-Pig Cerebral Cortex," *British Journal of Pharmacology*, 123 (Proc. Suppl.): 195p (1998). Meeting of the British Pharmacological Society Held Jointly with the Dutch Pharmacological Society (Dec. 10-12, 1997) XP008032489.

Sullivan, G. et al., "Role of A2A Adenosine Receptors in Inflammation," *Drug Development Research*, 45(3/4):103-12 (1998) XP000978332.

Ueeda, M. et al., "2-Alkoxyadenosines: Potent and Selective Agonists at the Coronary Artery A2 Adenosine Receptor," *Journal of Medicinal Chemistry*, 34:1334-9 (1991) XP002225574.

Ueeda, M. et al., "2-Aralkoxyadenosines: Potent and Selective Agonists at the Coronary Artery A2 Adenosine Receptor," *Journal of Medicinal Chemistry*, 34(4):1340-4 (1991) XP004088461.

Umino, T. et al., "Nucleosides and Nucleotides. 200. Reinvestigation of 5'-N-Ethylcarboxamidoadenosine Derivatives: Structure-Activity Relationships for P(3) Purinoceptor-Like Proteins," *Journal of Medicinal Chemistry*, 44:208-14 (2001) XP002366162.

Vittori, S. et al., "2-Alkenyl and 2-Alkyl Derivatives of Adenosine and Adenosine-5'-N-Ethyluronamide: Different Affinity and Selectivity of E- and Z-Diastereomers at A2A Adenosine Receptors," *Journal of Medicinal Chemistry*, 39:4211-7 (1996) XP002366163.

International Search Report for PCT/GB2003/05379, dated Mar. 31, 2004.

Ali Akbar Nekooeian et al., "Effects of adenosine $a_{2a}$ receptor agonist, cgs 21680, on blood pressure, cardiac index and arterial conductance in anaesthetized rats", 1996, European Journal of Pharmacology, vol. 307, pp. 163-169.

R.A.A. Mathôt et al., "Pharmacokinetic-haemodynamic relationships of 2-chloroadenosine at adenosine $A_1$ and $A_{2a}$ receptors in vivo", 1996, British Journal of Pharmacology, vol. 118, No. 2, pp. 369-377.

John R. Keddie et al., "In vivo characterisation of ZM 241385, a selective adenosine $A_{2a}$ receptor antagonist", 1996, European Journal of Pharmacology, vol. 301, pp. 107-113.

Randy L. Webb et al., "Development of Tolerance to the Antihypertensive Effects of Highly Selective Adenosine $A_{2a}$ Agonists upon Chronic Administration", 1993, The Journal of Pharmacology and Experimental Therapeutics, vol. 267, pp. 287-295.

R.L. Webb et al., "Cardiovascular Effects of Adenosine $A_2$ Agonists in the Conscious Spontaneously Hypertensive Rat: A Comparative Study of Three Structurally Distinct Ligands", 1991, The Journal of Pharmacology and Experimental Therapeutics, vol. 259, pp. 1203-1212.

C. Casati et al., "Telemetry Monitoring of Hemodynamic Effects Induced Over Time by Adenosine Agonists in Spontaneously Hypertensive Rats", 1995, The Journal of Pharmacology and Experimental Therapeutics, Vo. 275, pp. 914-919.

Erminio Bonizzoni et al., "Modeling Hemodynamic Profiles by Telemetry in the Rat, A Study With $A_1$ and $A_{2a}$ Adenosine Agonists", 1995, Hypertension, vol. 25, No. 4, Part 1, pp. 564-569.

Cristina Alberti et al., "Mechanism and Pressor Relevance of the Short-Term Cardiovascular and Renin Excitatory Actions of the Selective $A_{2a}$-Adenosine Receptor Agonists", 1997, Journal of Cardiovascular Pharmacology, vol. 30, No. 1, pp. 320-324.

Kaul & Daftari, "Marine pharmacology: bioactive molecules from the sea", Annual Review of Pharmacology and Toxicology, 26:117-142 (1986).

Kaul, "Biomedical potential of the sea", Pure and Applied Chemistry, 54:1963-1972 (1982).

Davies et al., "Displacement of [$^3$H] diazepam binding in rat brain by dipyridamole and by 1-methylisoguanosine, a marine natural product with muscle relaxant activity", Life Sciences 26:1089-1095 (1980).

Herrick-Davis et al., European J. Pharmacol. 162:365-369 (1989).

Field et al, "Gabapentin (neurontin) and S-(+)-3-isobutylgaba represent a novel class of selective antihyperalgesic agents," British Journal of Pharmacology, 121(8), 1513-1522 (1997).

E. Huttemann et al, "$R_a$ Adenosine receptors in human platelets," Naunyn-Schmiedeberg's Archives of Pharmacology, 1984, vol. 325:226-233.

T Trost & U Schwabe, "Adenosine Receptors in Fat Cells. Identification by (−)-N6-[3H] phenylisopropyladenosine binding," Molecular Pharmacology, 1980, vol. 19:228-235.

U Schwabe & T Trost, "Characterization of Adenosine Receptors in Rat Brain by (−) [$^3$H]$N^6$-Phenylisopropyladenosine," Naunyn-Schmiedeberg's Archives of Pharmacology, 1980, vol. 313:179-187.

Ji et al., "[$^3$H] MRS 1754, a selective antagonist radioligand for $A_{2b}$ adenosine receptors," Biochemical Pharmacology, 2001, vol. 61:657-663.

Peter H. Wu and John W. Phillis, "Adenosine Receptors in Rat Brain Membranes: Characterization of High Affinity Binding of [$^3$H]-2-Chloroadenosine," Int. J. Biochem., 1984, vol. 14:399-404.

Pan et al, "Allosteric Adenosine Modulation to Reduce Allodynia," Anesthesiology, 2001, vol. 95(2), 416-420.

Rane et al, "Intrathecal Adenosine Administration," Anesthesiology, 1998, vol. 89(5), 1108-1115.

Buster, "The effect of adenosine receptor agonists on . . . in experimental bacterial meningitis," Abstracts of the Interscience Conference of Antimicrobial Agents and Chemotherapy, 1997 37:39.

J. Rieger et al., "Design, Synthesis, and Evaluation of Novel $A_{2A}$ Adenosine Receptor Agonists," J. Med. Chem 2001 44(4):531-539.

M. Matova et al., "QSAR analysis of 2-alkyloxy and 2-aralkyloxy adenosine $A_1$-and $A_2$-agonists," Eur J Med. Chem 1997 32:505-513.

Cristalli et al., "Inhibition of platelet aggregation by adenosine receptor agonists," Arch Pharmacol (1994) 349:644-650.

Takashi Umino et al., "Nucleosides and Nucleotides. 200. Reinvestigation of 5'-*N*-E thylcarboxamidoadenosine Derivatives: Structure-Activity Relationships for $P_3$ Purinoceptor-like Proteins[1]," J. Med. Chem 2011 44:208-214.

Maarten de Zwart et al., "5'-*N*-Substituted Carboxamidoadenosines as Agonists for Adenosine Receptors," J. Med. Chem 1999 42:1384-1392.

* cited by examiner

A)

B)

A)

B)

–□– Vehicle + Vehicle
–○– Vehicle + spongosine (1.2 p.o.)
–■– Nalox (1 s.c.) + Vehicle
–●– Nalox (1 s.c.) + spongosine (1.2 p.o.)

A)

B)

C)

USE OF SPONGOSINE FOR THE TREATMENT OF PAIN

CROSS REFERENCE TO RELATED APPLICATIONS

This application is a national phase filing under 35 U.S.C. §371 of international application number PCT/GB2003/005379, filed Dec. 9, 2003, which claims the benefit of priority of British application number 0228723.3, filed Dec. 9, 2002. The disclosures of the prior applications are considered part of (and are incorporated by reference in) the disclosure of this application.

TECHNICAL FIELD

This invention relates to an analgesic and to methods of preventing, treating, or ameliorating pain using the analgesic.

BACKGROUND

Pain has two components, each involving activation of sensory neurons. The first component is the early or immediate phase when a sensory neuron is stimulated, for instance as the result of heat or pressure on the skin. The second component is the consequence of an increased sensitivity of the sensory mechanisms innervating tissue which has been previously damaged. This second component is referred to as hyperlagesia, and is involved in all forms of chronic pain arising from tissue damage, but not in the early or immediate phase of pain perception.

Thus, hyperalgesia is a condition of heightened pain perception caused by tissue damage. This condition is a natural response of the nervous system apparently designed to encourage protection of the damaged tissue by an injured individual, to give time for tissue repair to occur. There are two known underlying causes of this condition, an increase in sensory neuron activity, and a change in neuronal processing of nociceptive information which occurs in the spinal cord. Hyperalgesia can be debilitating in conditions of chronic inflammation (e.g. rheumatoid arthritis), and when sensory nerve damage has occurred (i.e. neuropathic pain).

Two major classes of analgesics are known: (i) non steroidal anti-inflammatory drugs NSAIDs) and the related COX-2 inhibitors; and (ii) opiates based on morphine. Analgesics of both classes are effective in controlling normal immediate, or nociceptive pain. However, they are less effective against some types of hyperalgesic pain, such as neuropathic pain. Many medical practitioners are reluctant to prescribe opiates at the high doses required to affect neuropathic pain because of the side effects caused by administration of these compounds, and the possibility that patients may become addicted to them. NSAIDs are much less potent than opiates, so even higher doses of these compounds are required. However, this is undesirable because these compounds cause irritation of the gastrointestinal tract.

Adenosine A1 receptor agonists are known to act as powerful analgesics (Sawynok, Eur J Pharmacol. (1998) 347, 1-11), and adenosine A2A receptor agonists are known to act as anti-inflammatory agents. However, development of adenosine-based therapies has generally been precluded because they have unacceptable side effects. Selective A1 receptor agonists cause bradycardia, and A2A receptor agonists cause widespread vasodilation with consequent hypotension and tachycardia.

Spongosine is a compound that was first isolated from the tropical marine sponge, *Cryptotethia crypta* in 1945 (Bergmann and Feeney, J. Org. Chem. (1951) 16, 981, Ibid (1956) 21, 226). Spongosine was the first methoxypurine found in nature, and is also known as 2-methoxyadenosine, or 9H-purin-6-amine, 9-$\alpha$-D-arabinofuraosyl-2-methoxy.

The first biological activities of spongosine were described by Bartlett et al. (J. Med. Chem. (1981) 24, 947-954) who showed that this compound has muscle relaxant, hypothermic, hypotensive, and anti-inflammatory activity in rats (anti-inflammatory activity was assessed by inhibition of carrageenan-induced oedema in a rat paw).

The affinity of spongosine for the rat adenosine A1 and A2A receptors has been determined. The Kd values obtained were 340 nM for the A1 receptor and 1.4 $\mu$M for the A2A receptor (Daly et al., Pharmacol. (1993) 46, 91-100). In the guinea pig, the efficacy of spongosine was tested in the isolated heart preparation and the EC50 values obtained were 10 $\mu$M and 0.7 $\mu$M for the adenosine A1 and A2A receptors, respectively (Ueeda et al J Med Chem (1991) 34, 1334-1339). In the early 1990s the other adenosine receptors (the A2B and A3 receptors) were cloned, but the activity of spongosine at these receptors was never investigated. The low potency and poor receptor selectivity of this compound led to it being largely ignored as more and more potent and receptor selective novel compounds were synthesised.

SUMMARY AND DETAILED DESCRIPTION

There is, therefore, a need to provide analgesics which are sufficiently potent to control pain perception in neuropathic, inflammatory, and other hyperalgesic syndromes, and which do not have serious side effects or cause patients to become addicted to them.

It has surprisingly been found that spongosine when administered to mammals gives significant pain relief in conditions of increased pain sensitivity (such as neuropathic and inflammatory hyperalgesia), without causing the significant side effects expected from use of purine receptor agonists.

According to the invention there is provided use of spongosine in the manufacture of a medicament for the prevention, treatment, or amelioration of pain.

The term "spongosine" is used herein to include spongosine free base, or a pharmaceutically acceptable salt of spongosine.

Use of spongosine according to the invention is particularly concerned with the prevention, treatment, or amelioration of pain other than the early or immediate phase of pain as described above, and is especially concerned with the prevention, treatment, or amelioration of hyperalgesia.

There is also provided according to the invention a method of preventing, treating, or ameliorating pain (in particular hyperalgesia) which comprises administering spongosine to a subject in need of such prevention, treatment, or amelioration.

Spongosine has surprisingly been found to be effective in inhibiting pain perception in mammals suffering from neuropathic and inflammatory pain even when administered at doses expected to give concentrations well below those known to activate adenosine receptors. Thus, spongosine can treat neuropathic and inflammatory pain without causing the significant side effects associated with administration of other adenosine receptor agonists.

No analgesic effect on normal physiological nociception was observed after administration of spongosine.

Because hyperalgesia is a consequence of tissue damage, either directly to a sensory nerve, or to tissue innervated by a sensory nerve, there are many diseases or conditions in which pain perception includes a component of hyperalgesia.

Spongosine can be used as an anti-hyperalgesic for the prevention, treatment, or amelioration of hyperalgesia caused as a result of neuropathy, including bowel pain, back pain, cancer pain, HIV pain, phantom limb pain, post-operative pain, diabetic neuropathy, polyneuropathy, post-herpes neuralgia, and trigeminal neuralgia.

Other diseases or conditions involving damage to sensory nerves which contain a component of neuropathic pain include, pancreatic pain, pelvic/perineal pain, lower back pain, chest pain, cardiac pain, pelvic pain/PID, joint pain (for example, associated with tendonitis, bursitis, acute arthritis), neck pain, obstetric pain (labour or Caesarean-Section), chronic neuropathic pain, failed back surgery pain, post physical trauma pain (including pain caused by a gunshot wound, a road traffic accident, or a burn), scar tissue pain, acute herpes Zoster pain, acute pancreatitis breakthrough pain (cancer), or for the prevention, treatment, or amelioration of neuropathic or other pain caused by, or associated with, fibromyalgia, myofascial pain syndrome, osteoarthritis, rheumatoid arthritis, sciatica or lumbar radiculopathy, spinal stenosis, temporo-mandibular joint disorder, renal colic, dysmenorrhoea/endometriosis.

Spongosine can be used as an anti-hyperalgesic for the prevention, treatment, or amelioration of hyperalgesia caused as a result of inflammatory disease, including bowel pain, back pain, cancer pain, fibromyalgia, post-operative pain, osteoarthritis, and rheumatoid arthritis.

Other diseases or conditions in which hyperalgesia plays a prominent role in pain perception because they are associated with chronic inflammation include other arthritic conditions such as rheumatoid spondylitis, gouty arthritis, or asthma, chronic obstructive pulmonary disease, fibrosis, multiple sclerosis, sepsis, septic shock, endotoxic shock, gram negative shock, toxic shock, hemorrhagic shock, adult respiratory distress syndrome, cerebral malaria, organ transplant rejection, pain secondary to cancer, HIV, chronic pulmonary inflammatory disease, silicosis, pulmonary sarcosis, bone resorption diseases, reperfusion injury, graft v. host rejection, multiple sclerosis, myasthenia gravis, allograft rejections, fever and myalgia due to infection, AIDS related complex (ARC), keloid formation, scar tissue formation, Crohn's disease, ulcerative colitis and pyresis, irritable bowel syndrome, osteoporosis, cerebral malaria, bacterial meningitis, or adverse effects from amphotericin B treatment, interleukin-2 treatment, OKT3 treatment, or GM-CSF treatment.

The pain associated with many of the above diseases or conditions are relatively resistant to NSAIDs and opiates.

It will be appreciated that spongosine may be administered together with a pharmaceutically acceptable carrier, excipient, or diluent.

The appropriate dosage of spongosine will vary with the age, sex, and weight of the subject being treated, and the route of administration.

Preferably spongosine is administered at a dose that gives rise to plasma concentrations one fifth to one thousandth, preferably one fifth to one hundredth, of the minimum plasma concentration of spongosine that gives rise to bradycardia, hypotension or tachycardia side effects in animals of the same species as the subject to which the dose is to be administered.

Alternatively, it is preferred that spongosine is administered at a dose that is one fifth to one fiftieth, preferably one fifth to one tenth, of the minimum dose of spongosine that gives rise to bradycardia, hypotension or tachycardia side effects in animals of the same species as the subject to which the dose is to be administered.

Preferably spongosine is administered at a dose of less than 6 mg/kg, and preferably at least 0.01 mg/kg, more preferably at least 0.05 mg/kg, most preferably at least 0.1 mg/kg. More preferably spongosine is administered at a dose of 0.1 to 1 mg/kg, or 0.2 to 1 mg/kg.

Thus, preferred doses for a 70 kg human subject are less than 420 mg, preferably at least 0.7 mg, more preferably at least 3.5 mg, most preferably at least 7 mg. More preferably 7 to 70 mg, or 14 to 70 mg.

Spongosine may be administered by any suitable route, preferably orally, parenterally, sublingually, transdermally, intrathecally, or transmucosally.

Preferably spongosine is administered at a frequency of 2 or 3 times per day.

It has also been found that additive analgesic effects can be obtained if spongosine is administered with another analgesic agent. Thus, spongosine and the other analgesic agent can be administered to obtain a desired level of analgesic effect, each at a lower dose than would be required to achieve that level if either agent was administered alone. Because lower doses of each agent can be administered, side effects associated with administration of higher doses of the agents are reduced. Alternatively, an increased level of analgesic effect can be obtained by administering spongosine and the other analgesic agent at higher doses.

The preferred dosage of spongosine when administered with another analgesic agent is lower than a preferred dosage specified above for administration of spongosine alone.

It is believed that an additive analgesic effect is achieved if the other analgesic agent does not act in the same way as spongosine. Suitable other analgesic agents that may be administered with spongosine include opioid receptor agonists and partial agonists (such as morphine, diamorphine, fentanyl, buprenorphine, codeine, or derivatives thereof), cyclooxygenase inhibitors (such as aspirin, paracetamol, ibuprofen, diclofenac, or derivatives thereof), sodium or calcium channel modulators (such as lignocaine, or gabapentin), or Selective Serotonin Reuptake Inhibitors (SSRI's) (such as paxil).

Example 4 below shows that the anti-hyperalgesic properties of spongosine are unaffected by co-administration of the opioid receptor antagonist naloxone indicating that spongosine does not act via an opioid receptor. Example 5 below demonstrates the additive analgesic effects of co-administration of spongosine and gabapentin. Gabapentin is effective against neuropathic pain. It is expected that other analgesic agents that are designed to treat neuropathic pain may have additive analgesic effects with spongosine. Such agents include topamax, pregabalin, ziconitide, and cannabinoid derivatives.

DESCRIPTION OF DRAWINGS

Embodiments of the invention are described in the following examples with reference to the accompanying drawings in which.

EXAMPLES

Example 1

Figure 1:
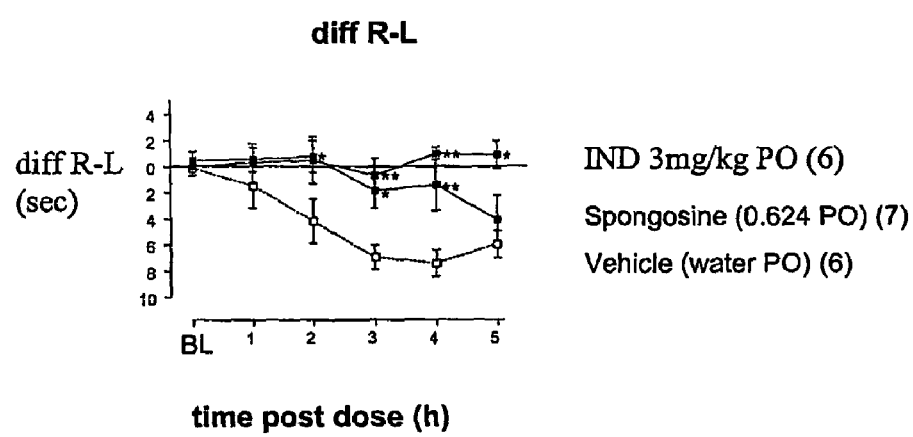
FIG. 1 shows the anti-hyperalgesic actions of spongosine (0.6 mg/kg p.o.) on carrageenan induced hyperalgesia. A: time course (*$p<0.05$, **$p<0.01$ versus vehicle (Sidak's), $p>0.05$ versus BL over 5 hrs for Spongosine and IND (Dunnett's)); B: dose dependency of the anti-hyperalgesic effect.
Figure 1:
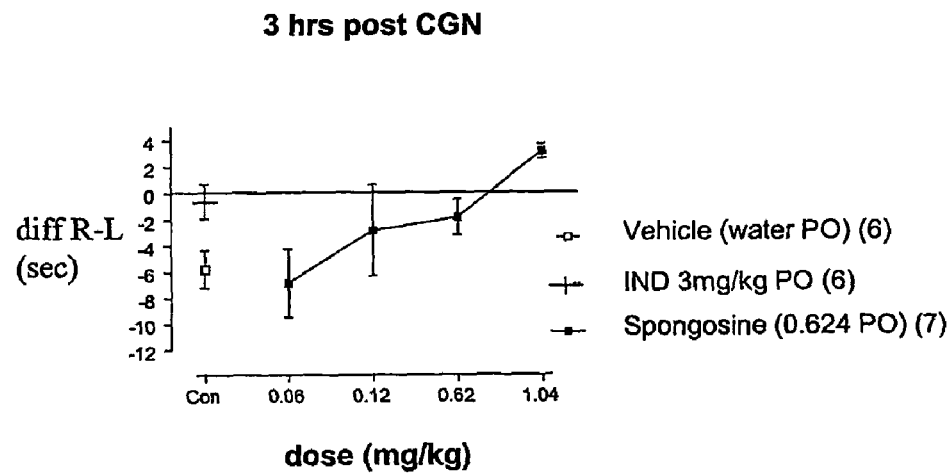

FIG. 1: A. Spongosine (0.624 mg/kg p.o.) inhibits carrageenan (CGN) induced thermal hyperalgesia (CITH) with comparable efficacy to indomethacin (3 mg/kg, po). B. Concentration-response relationship for Spongosine at 3 hrs post dosing. Carrageenan (2%, 10 microliters) was administered into the right hind paw. A heat source was placed close to the treated and untreated hind paws, and the difference in the paw withdrawal latencies is shown. Spongosine was administered at the same time as carrageenan.

Example 2

Figure 2:
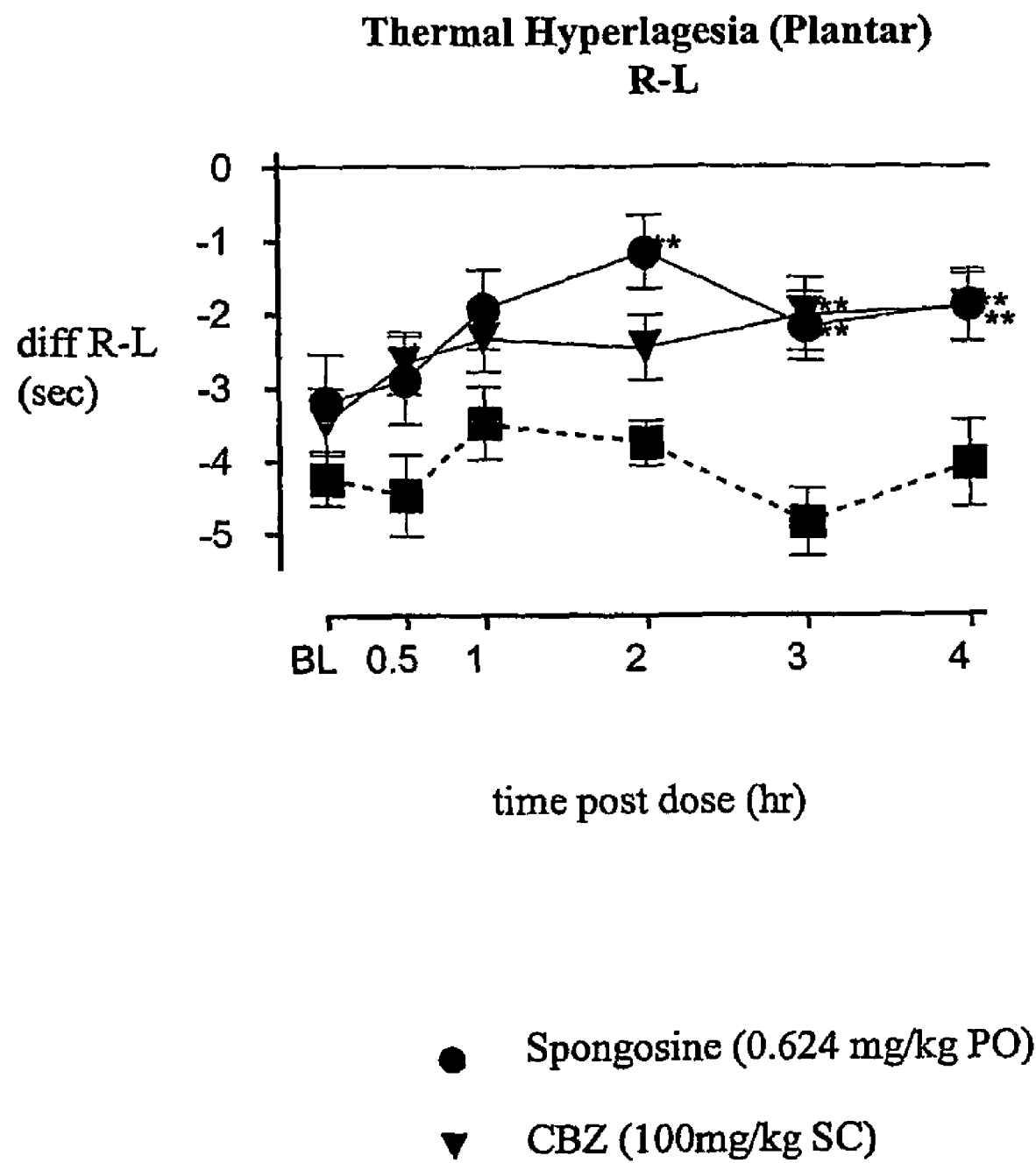
FIG. 2 shows the anti-hyperalgesic actions of spongosine (0.6 mg/kg p.o.) in the chronic constriction injury model of neuropathic pain (*$p<0.05$, **$p<0.01$ vs veh (ANOVA Sidak's)

FIG. 2: Spongosine (0.624 mg/kg p.o.) inhibits thermal hyperalgesia caused by chronic constriction injury of the rat sciatic nerve. Under anaesthesia the sciatic nerve was displayed in the right leg, and four loose ligatures tied round the nerve bundle. After approximately two weeks the rats developed thermal hyperalgesia in the operated leg as judged by the difference in paw withdrawal latencies of the right and left paws. Administration of spongosine reduced the hyperalgesia as shown by the reduction in the difference between the withdrawal latencies. Spongosine was as, or more, effective than carbamazepine (CBZ, 100 mg/kg s.c.)

Example 3

Figure 3:
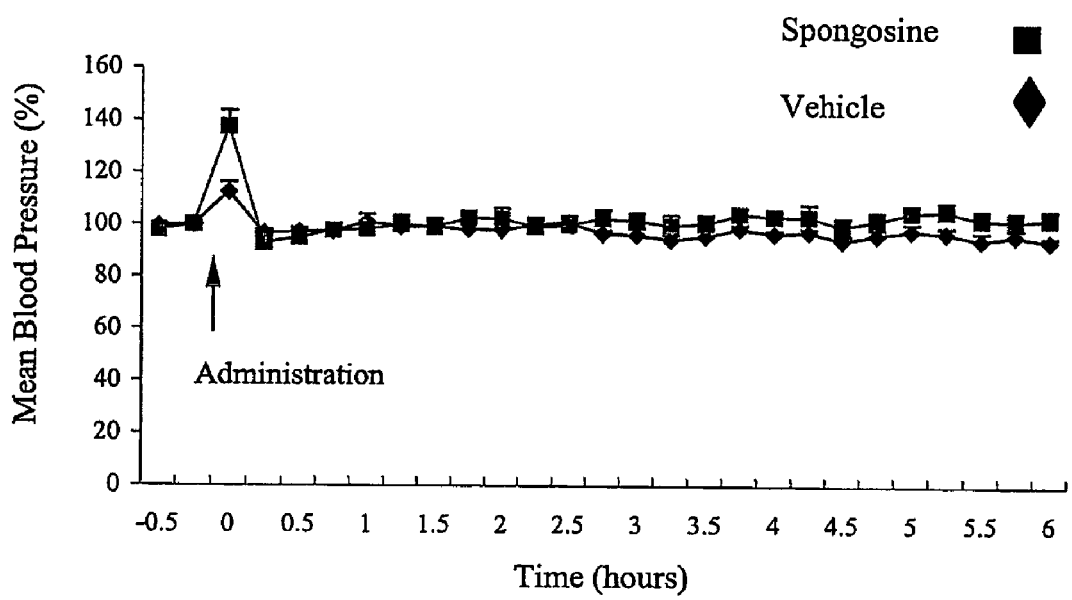
FIG. 3 shows the effect of spongosine (0.6 mg/kg p.o.) on A: blood pressure in normal rats; B: heart rate.
Figure 3:
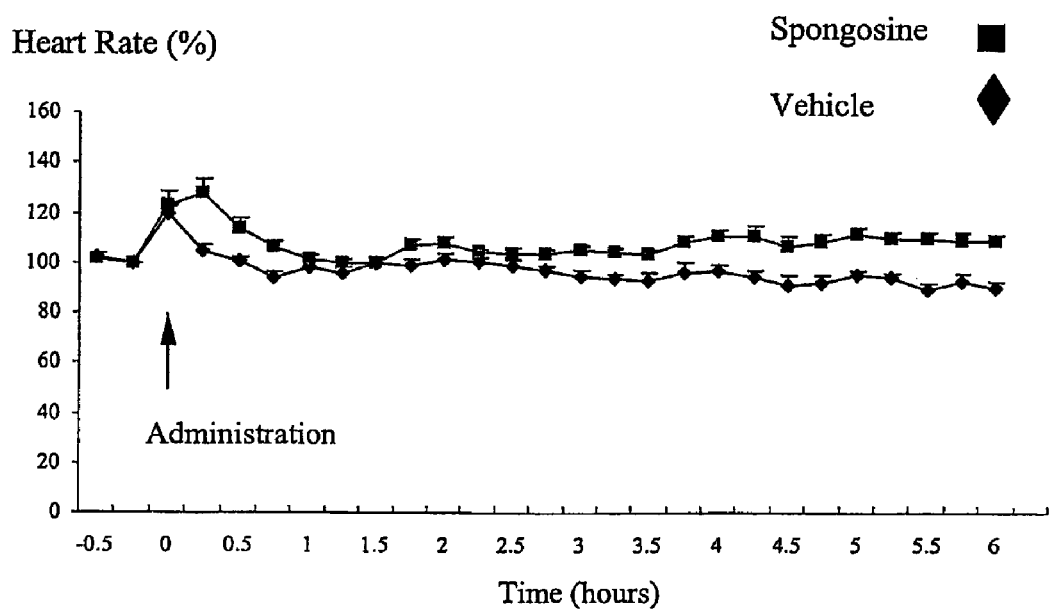

FIG. 3: Spongosine (0.624 mg/kg p.o.) has no significant effect on blood pressure or heart rate. An implantable radiotelemetry device was placed in the abdominal cavity of 6 rats per group. The pressure catheter of the device was inserted in the abdominal aorta and two electrodes tunnelised under the skin in a lead II position (left side of abdominal cavity/right shoulder). Individual rats were placed in their own cage on a radioreceptor (DSI) for data acquisition. A: blood pressure, B; heart rate.

Example 4

Figure 4:
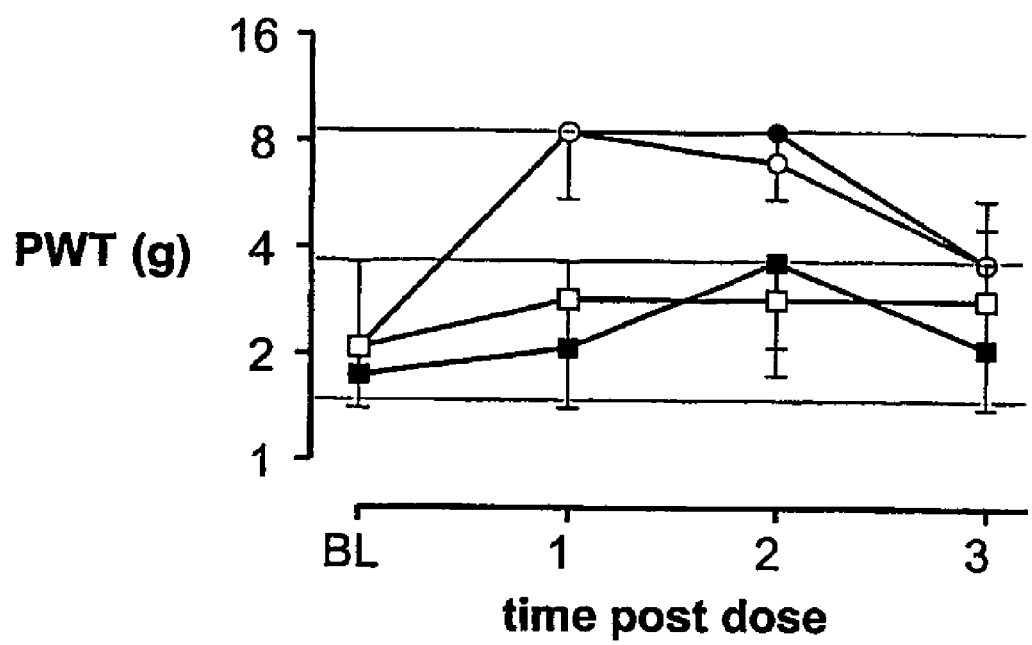
FIG. 4 shows the effect of spongosine (0.6 mg/kg p.o.) in the presence and absence of naloxone in a model of neuropathic pain.

FIG. 4: Spongosine (1.2 mg/kg p.o.) inhibits static allodynia in a model of neuropathic pain, both in the presence and absence of naloxone (1 mg/kg s.c.). Administration of spongosine reduced the hyperalgesia as shown by the increased paw withdrawal threshold (PWT) in the presence and absence of naloxone. Veh: vehicle.

Example 5

Figure 5:
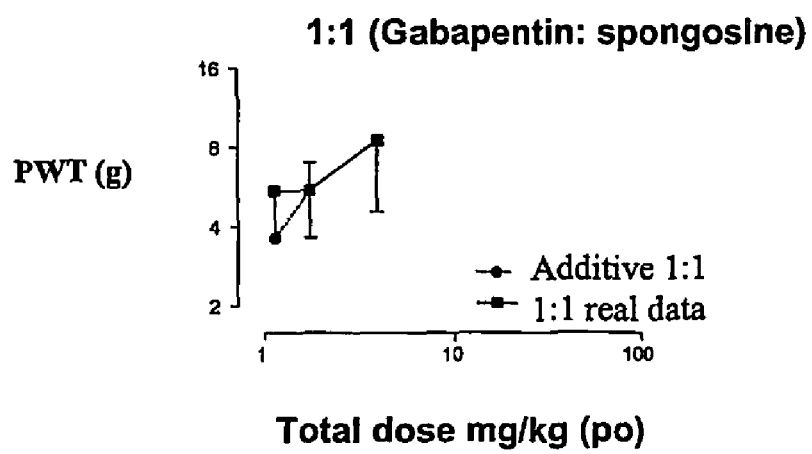
FIG. 5 shows the additive effect of spongosine and gabapentin in a model of neuropathic pain.
Figure 5:
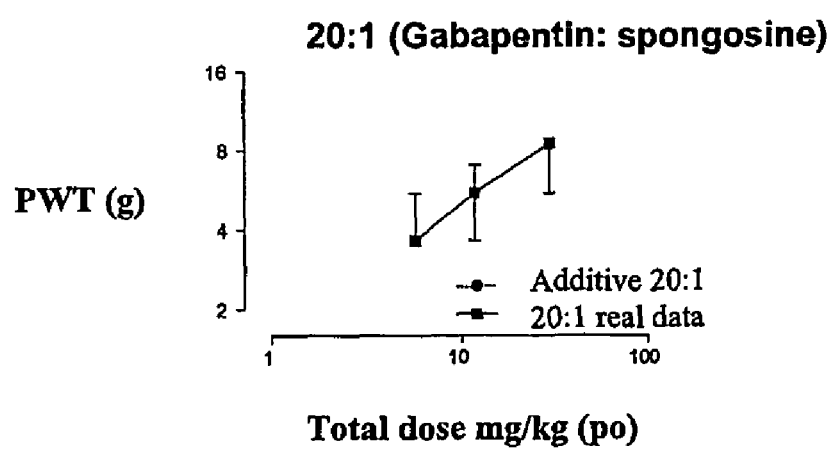
Figure 5:
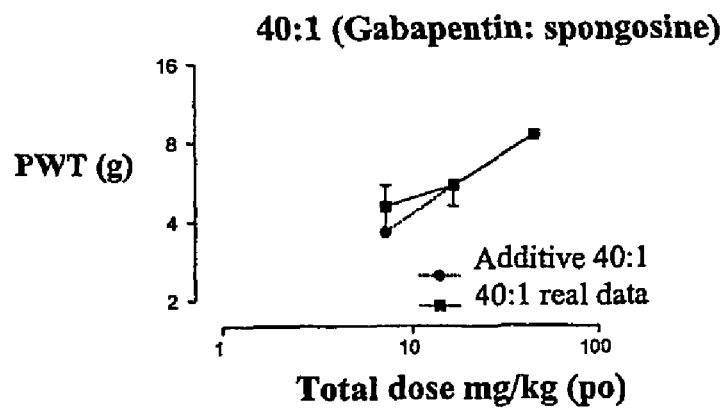

FIG. 5: Spongosine and gabapentin inhibit static allodynia in a model of neuropathic pain. Spongosine and gabapentin were administered (p.o.) in different proportions as indicated in the drawing. The total dose administered is shown on the horizontal axis, and the paw withdrawal threshold (PWT) on the vertical axis. The predicted anti-hyperalgesic effect (derived from the dose response curves obtained with each agent alone) if the effects of the two compounds are additive is shown (●). The observed effects are indicated by (■). It is apparent that the observed effects are not significantly different from those predicted by additivity.

Spongosine is effective in inhibiting pain perception in mammals suffering from neuropathic and inflammatory pain even when administered at doses expected to give concentrations well below those known to activate adenosine receptors. At these doses it can be seen that neither the heart A1 receptors nor the vascular A2A receptors are sufficiently stimulated to cause a change in the cardiovascular status of the animals.

Spongosine can therefore be used as an anti-hyperalgesic which can be administered orally for the treatment of hyperalgesia caused as a result of neuropathy or inflammatory disease, including bowel pain, back pain, cancer pain, fibromyalgia, HIV pain, phantom limb pain, osteoarthritis, rheumatoid arthritis, post-herpes neuralgia, trigeminal neuralgia, polyneuropathy, diabetic neuropathy and post-operative pain.

The invention claimed is:
1. A method of treating pain which comprises administering a therapeutically effective amount of spongosine (2-methoxyadenosine) or a pharmaceutically acceptable salt thereof to a human subject in need of such treatment.
2. The method of claim 1, wherein spongosine or a pharmaceutically acceptable salt thereof is administered orally.
3. The method of claim 1, wherein the pain is hyperalgesia.
4. The method of claim 3, wherein the hyperalgesia is caused by or associated with sensory nerve damage.
5. The method of claim 3, wherein the hyperalgesia is caused by or associated with inflammation.
6. The method of claim 1, wherein the pain is caused by or associated with sensory nerve damage.
7. The method of claim 1, wherein the pain is caused by or associated with inflammation.
8. The method of claim 1, wherein spongosine or a pharmaceutically acceptable salt thereof is administered at a dose that gives rise to plasma concentrations one fifth to one thousandth of the minimum plasma concentration of spongosine or a salt thereof that gives rise to bradycardia, hypotension or tachycardia side effects in the human subject.
9. The method of claim 8, wherein the dose gives rise to plasma concentrations one fifth to one hundredth of the minimum plasma concentration of spongosine or a salt thereof that gives rise to the side effects.
10. The method of claim 1, wherein spongosine or a pharmaceutically acceptable salt thereof is administered at a dose that is one fifth to one fiftieth of the minimum dose of spongosine or a salt thereof that gives rise to bradycardia, hypotension or tachycardia side effects in the human subject.
11. The method of claim 10, wherein the dose is one fifth to one tenth of the minimum dose of spongosine or a salt thereof that gives rise to the side effects.
12. The method of claim 1, wherein spongosine or a pharmaceutically acceptable salt thereof is administered at a dose of less than 6 mg/kg.
13. The method of claim 1, wherein spongosine or a pharmaceutically acceptable salt thereof is administered at a dose of at least 0.01 mg/kg.
14. The method of claim 1, wherein spongosine or a pharmaceutically acceptable salt thereof is administered at a dose of at least 0.1 mg/kg.
15. The method of claim 14, wherein spongosine or a pharmaceutically acceptable salt thereof is administered at a dose of 0.1 to 1 mg/kg.
16. The method of claim 1, wherein spongosine or a pharmaceutically acceptable salt thereof is administered orally, parenterally, sublingually, transdermally, intrathecally, or transmucosally.

17. The method of claim 1, wherein spongosine or a pharmaceutically acceptable salt thereof is administered at a frequency of 2 or 3 times per day.

18. The method of claim 1, wherein the pain is associated with or caused by thermal hyperalgesia.

19. A method of treating pain which comprises administering spongosine (2-methoxyadenosine) or a pharmaceutically acceptable salt thereof to a human subject in need of such treatment, wherein the spongosine or the salt thereof is administered at a dose that gives rise to plasma concentrations one fifth to one thousandth of the minimum plasma concentration of spongosine or the salt thereof that gives rise to bradycardia, hypotension or tachycardia side effects in humans.

20. The method of claim 19, wherein the pain is hyperalgesia.

21. The method of claim 20, wherein the hyperalgesia is caused by or associated with sensory nerve damage.

22. The method of claim 20, wherein the hyperalgesia is caused by or associated with chronic inflammation.

23. The method of claim 19, wherein the pain is caused by or associated with sensory nerve damage.

24. The method of claim 19, wherein the pain is caused by or associated with inflammation.

25. The method of claim 19, wherein the dose gives rise to plasma concentrations one fifth to one hundredth of the minimum plasma concentration of spongosine or the salt thereof that gives rise to the side effects.

26. The method of claim 19, wherein spongosine or a pharmaceutically acceptable salt thereof is administered at a dose that is one fifth to one fiftieth of the minimum dose of spongosine or the salt thereof that gives rise to bradycardia, hypotension or tachycardia side effects in humans.

27. The method of claim 19, wherein spongosine or a pharmaceutically acceptable salt thereof is administered orally.

28. A method of treating pain which comprises administering spongosine (2-methoxyadenosine) or a pharmaceutically acceptable salt thereof to a human subject in need of such treatment comprising administering a therapeutically effective amount of spongosine or a pharmaceutically acceptable salt thereof to the human subject, wherein spongosine or the salt thereof is administered at a dose of less than 6 mg/kg.

29. The method of claim 28, wherein spongosine or a pharmaceutically acceptable salt thereof is administered at a dose of at least 0.01 mg/kg.

30. The method of claim 28, wherein spongosine or a pharmaceutically acceptable salt thereof is administered at a dose of at least 0.1 mg/kg.

31. The method of claim 28, wherein spongosine or a pharmaceutically acceptable salt thereof is administered at a dose of 0.1 to 1 mg/kg.

32. The method of claim 28, wherein spongosine or a pharmaceutically acceptable salt thereof is administered orally.

33. A method of treating pain which comprises administering 3.5 to 70 mg of spongosine (2-methoxyadenosine) or a pharmaceutically acceptable salt thereof to a human subject in need of such treatment.

34. The method of claim 33 wherein the spongosine or a pharmaceutically acceptable salt thereof is administered 2 or 3 times per day.

35. The method of claim 33, wherein 3.5 to 42 mg of spongosine or a pharmaceutically acceptable salt thereof is administered to the human subject.

36. A method of treating pain which comprises administering a therapeutically effective amount of spongosine (2-methoxyadenosine) or a pharmaceutically acceptable salt thereof to a human subject in need of such treatment, wherein spongosine or the salt thereof is administered at a dose that gives rise to plasma concentrations one fifth to one thousandth of the minimum plasma concentration of spongosine or the salt thereof that gives rise to bradycardia, hypotension or tachycardia side effects in the human subject and is administered at a dose of at least 0.01 mg/kg.

37. The method of claim 36, wherein spongosine or a pharmaceutically acceptable salt thereof is administered orally.

38. A method of treating pain which comprises administering spongosine (2-methoxyadenosine) or a pharmaceutically acceptable salt thereof to a human subject in need of such treatment, wherein the spongosine or salt thereof is administered at a dose of 0.01 mg/kg to 1 mg/kg.

39. The method of claim 38 wherein the spongosine or the salt thereof is administered 2 or 3 times per day.

40. The method of claim 38, wherein spongosine or a pharmaceutically acceptable salt thereof is administered orally.

* * * * *